US012616673B2

(12) United States Patent (10) Patent No.: US 12,616,673 B2
Fazi et al. (45) Date of Patent: May 5, 2026

(54) COMPOUNDS FOR USE IN THE TREATMENT OF LEUKEMIA

(71) Applicant: UNIVERSITA' DEGLI STUDI DI ROMA "LA SAPIENZA", Rome (IT)

(72) Inventors: Francesco Fazi, Rome (IT); Silvia Masciarelli, Rome (IT)

(73) Assignee: UNIVERSITA' DEGLI STUDI DI ROMA "LA SAPIENZA", Rome (IT)

( * ) Notice: Subject to any disclaimer, the term of this patent is extended or adjusted under 35 U.S.C. 154(b) by 759 days.

(21) Appl. No.: 17/759,546

(22) PCT Filed: Jan. 28, 2021

(86) PCT No.: PCT/IB2021/050674
§ 371 (c)(1),
(2) Date: Jul. 27, 2022

(87) PCT Pub. No.: WO2021/152501
PCT Pub. Date: Aug. 5, 2021

(65) Prior Publication Data
US 2023/0073499 A1      Mar. 9, 2023

(30) Foreign Application Priority Data
Jan. 29, 2020      (IT) ........................ 102020000001732

(51) Int. Cl.
| *A61K 31/203* | (2006.01) |
| *A61K 31/375* | (2006.01) |
| *A61K 31/4045* | (2006.01) |
| *A61K 31/69* | (2006.01) |
| *A61K 33/36* | (2006.01) |
| *A61K 45/06* | (2006.01) |
| *A61P 35/02* | (2006.01) |

(52) U.S. Cl.
CPC .......... *A61K 31/203* (2013.01); *A61K 31/375* (2013.01); *A61K 31/4045* (2013.01); *A61K*

*31/69* (2013.01); *A61K 33/36* (2013.01); *A61K 45/06* (2013.01); *A61P 35/02* (2018.01)

(58) Field of Classification Search
CPC .... A61K 31/203; A61K 31/375; A61K 33/36; A61P 35/02
See application file for complete search history.

(56) References Cited

FOREIGN PATENT DOCUMENTS

| WO | 2015101618 A1 | 7/2015 |
| WO | WO 2020117868 | * 6/2020 |

OTHER PUBLICATIONS

Liang et al., Pediatric Blood and Cancer, Nov. 2018, vol. 65, Supp. Supplement 2, pp. S182. Abstract No. PO-197.*
Noguera et al., Oncotarget 2017, pp. 32550-32565.*
Goodman & Gilman's The Pharmacological Basis of Therapeutics regarding possible drug-drug interactions (9th ed, 1996) p. 51.*
Masciarelli et al., "Retinoic acid synergizes with the unfolded protein response and oxidative stress to induce cell death in FLT3-ITD + AML", Blood Advances, 2019, vol. 3, No. 24, pp. 4155-4160.
Larrue et al., "Proteasome inhibitors induce FLT3-ITD degradation through autophagy in AML cells", Blood, 2016, vol. 127, No. 7, pp. 882-892.
International Search Report and Written Opinion for Corresponding International Application No. PCT/IB2021/050674, 12 pages, May 20, 2021.

* cited by examiner

*Primary Examiner* — Kortney L. Klinkel
(74) *Attorney, Agent, or Firm* — Lucas & Mercanti, LLP

(57) ABSTRACT

The present invention belongs to the field of cancer therapy and relates to a composition or product comprising at least one retinoid compound, at least one arsenic compound and at least one proteasome inhibitor, for use in the treatment of acute myeloid leukemia (AML) where the tumor cells are positive for the FLT3-ITD mutation.

7 Claims, 10 Drawing Sheets

Specification includes a Sequence Listing.

PATIENT 1

PATIENT 2

MV-4-11

MOLM-13

CNX/DNA

Isolated nuclei

DNA                    Nrf-2

SEQUENCE LISTING

```
<160> NUMBER OF SEQ ID NOS: 13

<210> SEQ ID NO 1
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 1
gagtccgcag caggtgc                                                    17

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 2
tgtgacctct gctggttctg                                         20

<210> SEQ ID NO 3
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 3
gagtccgcag caggtgc                                            17

<210> SEQ ID NO 4
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 4
tccttctggg tagacctctg ggag                                    24

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
tagcgtatgg tgctgctgtc                                         20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
tttgtcaggg gtctttcacc                                         20

<210> SEQ ID NO 7
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 7
gtgaagaaac ctcatcgtta caggcctggt                              30

<210> SEQ ID NO 8
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 8
ctgcaaagca ccaatagctg cactctggaa                              30

<210> SEQ ID NO 9

-continued

```
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 9
tcatgaggaa ctttcagaag gg                                              22

<210> SEQ ID NO 10
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 10
tgcgctcaat ctcctcct                                                   18

<210> SEQ ID NO 11
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 11
aaggtcggag tcaacggatt tggtc                                           25

<210> SEQ ID NO 12
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 12
acatcgctca gacaccatg                                                  19

<210> SEQ ID NO 13
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 13
tgtagttgag gtcaatgaag gg                                              22
```

COMPOUNDS FOR USE IN THE TREATMENT OF LEUKEMIA

CROSS-REFERENCE TO RELATED APPLICATIONS

This application is a 371 of PCT/IB2021/050674, filed Jan. 28, 2021, which claims the benefit of Italian Patent Application No. 102020000001732, filed Jan. 29, 2020.

REFERENCE TO A SEQUENCE LISTING SUBMITTED ELECTRONICALLY VIA EFS-WEB

The content of the electronically submitted sequence listing, file name: 128-1262_SeqListing.txt; size: 4 KB; and date of creation Jul. 5, 2022, filed herewith, is incorporated herein by reference in its entirety.

FIELD OF THE INVENTION

The present invention belongs to the field of cancer therapy and relates to a composition or product comprising at least one retinoid compound, at least one arsenic compound and at least one proteasome inhibitor, for use in the treatment of acute myeloid leukemia (AML) where the tumor cells are positive for the FLT3-ITD mutation (FLT3-ITD+ AML). Preferably, the composition or product of the invention comprises:

a) all-trans retinoic acid (ATRA) and/or derivatives thereof and/or pharmaceutically acceptable salts thereof,
b) arsenic trioxide (ATO) and
c) the proteasome inhibitor Bortezomib (Btz).

BACKGROUND OF THE INVENTION

Acute myeloid leukemia (AML) is the most frequent non-paediatric acute leukemia. At present, first-line therapy is based on chemotherapy, whether or not associated with bone marrow transplantation, with 40-50% and 10-15% cure rates in adult and older patients, respectively. It is therefore clear that more effective innovative therapeutic approaches are needed.

The endoplasmic reticulum (ER) is the cellular organelle responsible for the maturation and correct folding of proteins that travel through the secretory pathway, i.e., secreted proteins and membrane-residing proteins. Disruption in the balance of this organelle (for example, due to the presence of mutated proteins, alterations in the cell's redox balance or physiological calcium concentrations) results in accumulation of non-properly matured proteins in the ER. This phenomenon is called ER stress. The cellular response to ER stress, defined as "Unfolded Protein Response" (UPR), plays a fundamental role in maintaining cellular protein homeostasis (proteostasis). The idea of interfering with proteostasis to promote cancer cell death has been widely described in the case of multiple myeloma (MM)[1]. In fact, the success of the proteasome inhibitors currently used in MM therapy can be attributed, at least in part, to the fact that the secretory pathway, whose function strictly depends on an efficient proteasome system, is very active in plasma cells[2]. The present authors therefore hypothesized that a similar strategy could be used to target AML cells.

AMLs make up a group of heterogeneous diseases caused by an arrest of myeloid progenitor differentiation due to numerous and different genetic alterations, which result in the production of mutant proteins or fusions of different proteins. Cells of a particular type of AML, i.e., acute promyelocytic leukemia (APL), can be induced to complete granulocyte differentiation by pharmacological doses of all-trans retinoic acid (ATRA). This differentiation requires an increase in the production of secretory proteins, thereby generating a physiological ER stress.

The present authors have previously demonstrated that this increase in the level of ER activity is sufficient to make differentiation-induced APL cells sensitive to doses of a drug, i.e., Tunicamycin (Tm), that impairs the maturation ability of the ER proteins, which instead do not cause lethal effects in the same cells not treated with ATRA[3]. Tunicamycin is a mixture of homologous nucleoside antibiotics which inhibits the UDP-HexNAc:polyprenol-P HexNAc-1-P enzyme family. In eukaryotes, this includes the GlcNAc phosphotransferase (GPT) enzyme, which catalyzes the transfer of N-acetylglucosamine-1-phosphate from UDP-N-acetylglucosamine to dolichol phosphate in the first step of glycoprotein synthesis. Tunicamycin blocks N-linked glycosylation (N-glycans), and treatment of cultured human cells with tunicamycin in high doses causes cell cycle arrest in the G1 phase.

Furthermore, the addition of Arsenic Trioxide (ATO), which causes oxidative stress, to the combination of ATRA and Tm significantly increases the lethal effect on APL cells[3]. At present, ATRA and ATO are the first-line therapy for particular APL subgroups[4]; the most important feature of the present authors' previous work[3] is that the synergistic effect of the three drugs, i.e., ATRA, Tm and ATO, allows the use of low doses of each of them, possibly reducing the risk of a generic toxicity. In fact, in support of this hypothesis, the present authors have shown that the triple combination is capable of reducing the clonogenic ability of primary APL cells isolated from the bone marrow of patients and treated in culture ex vivo, without however affecting the proliferation ability of hematopoietic progenitors isolated from healthy donors[3].

Later, the goal was to try to apply this strategy to other types of AML. Only APL cells are able to complete granulocyte differentiation when stimulated with pharmacological doses of ATRA. However, the above study[3] showed that the oncogenic fusion protein characteristic of APL forms high molecular weight protein aggregates in cells treated with ATRA and Tm, thereby generating further disruption in the secretory pathway compartment. Since many other subtypes of AML are characterized by the expression of mutant and fusion proteins that could be an intrinsic cause of proteostasis impairment, the present authors hypothesized that this could be at the basis of a greater sensitivity to the pharmacological induction of further cell stress in AML cells expressing these proteins, thus creating a rationale for applying the same strategy used in the case of APL. In fact, protein products derived from chromosomal alterations, such as translocations and duplications, are frequently the cause of proteostasis impairment, due to the impossibility of being correctly folded. In particular, the present authors focused on AMLs expressing the internal tandem duplication (ITD) in the FMS-like tyrosine kinase 3 (FLT3) receptor tyrosine kinase. FLT3-ITD is particularly interesting in this context because, since it is a protein residing in the plasma membrane, it is folded in the ER, and it is known from the literature that the ITD mutation prevents its correct folding and causes its partial retention in the ER[5]. In addition, the FLT3-ITD mutation is one of the most frequent mutations in adult AML patients, detected in approximately 30% of cases, associated with numerous other earlier mutations in AML development, and correlated with poor prognosis[6]. The present authors have also shown that treatment of FLT3-ITD positive (FLT3-ITD$^+$) AML cell lines with the same combination of low doses of ATRA, Tm and ATO causes cell death. Moreover, the same treatment causes a significant decrease in the clonogenic ability of primary cells isolated from the bone marrow of FLT3-ITD$^+$ AML patients, without however affecting the same ability of cells isolated from healthy donors[7].

Currently, the only molecular-targeted therapy for AMLs is based on ATRA and ATO and is applied to APLs. Although, after decades with no particular novelty in AML treatment, significant developments have occurred in recent years, most notably the FDA approval of an FLT3 tyrosine kinase inhibitor (TKI) for treatment of FLT3-ITD$^+$ AMLs in 2017 (1st generation)[8] and another in 2018 (2nd generation)[9], in general, the results obtained with these drugs are not satisfactory. In fact, since the FLT3-ITD mutation leads to a very negative prognosis and numerous scientific studies show that it is its kinase activity that causes the leukemogenic characteristics, the last few years have seen the development of many TKIs. Several clinical trials were carried out with different TKIs, either used as single therapeutic agents or in combination with chemotherapy or with chemotherapy associated with molecular-targeted therapies, mostly inhibitors of anti-apoptotic molecules, but responses were incomplete and characterized by the onset of resistance[10-12]. Several FLT3-ITD targeting strategies were adopted, which were correlated with its structural defects or with aberrantly activated transduction pathways due to mutation. However, to our knowledge, none of these include the triple combination of ATRA, Bortezomib (Btz) and ATO. FLT3-ITD$^+$ AML cell lines and primary cells were found to be particularly sensitive to Btz which causes FLT3-ITD degradation by autophagy and subsequent cell death[13]. Importantly, however, the doses of Btz used in this study are at least 6.5 times higher than those used in combination with ATRA and ATO in the present application. Tsitsipatis and co-workers inhibited FLT3-ITD glycosylation with Tm, generating ER stress and cell death, also describing a synergistic effect with the first generation FLT3 inhibitor AC220 (Quizartinib)[14]. In this study too, however, the amount of Tm used in combination with the TKI on ex vivo primary AML cells is 10 times higher than that used by the present authors in combination with ATRA and ATO. Another study showed that the increase in oxidative stress enhances the action of TKIs: agents that increase the amount of reactive oxygen species (ROS) amplify their effectiveness[15]. Ma and co-workers also showed that ATRA acts synergistically with TKIs to eliminate leukemic stem cells, in vitro and in vivo, in a murine model. These authors hypothesize that ATRA, which plays a fundamental role in the physiology of hematopoietic differentiation, activates quiescent leukemic stem cells, making them more sensitive to TKIs[16]; in this study, the dose of ATRA used is 10 times higher than that proposed in the combination according to the present application. Lastly, Wang and co-workers tested a combination of ATRA and ATO on FLT3-ITD$^+$ AML cell lines, based on the fact that these drugs are able to eradicate APL even in the presence of clones with this mutation. Indeed, the authors showed that the combination of ATRA and ATO, used at higher doses than the reference therapeutic doses in APL, inhibits FLT3-ITD-activated signal transduction, causing cell death of non-APL AML lines[17].

WO2015/101618 claims the use of an arsenic compound with at least one retinoid compound for the treatment of NMP1-mutated AMLs. In particular, the invention is directed to AMLs with the NMP-1 mutation, but negative for the FLT3-ITD mutation.

Overall, these studies indicate the scientific community's high interest in identifying a drug combination which can target the FLT3-ITD mutation. Furthermore, a series of communications at the recent congress of the European School of Hematology (ESH meeting, Estoril, Portugal, 23-26 Oct. 2019) showed that the use of TKIs against FLT3-ITD causes the development of resistant leukemic clones, which have additional mutations in other oncogenes[18], stressing the fact that the future of FLT3-ITD$^+$ AML therapy is probably in the combination of multiple drugs that insist on different cell systems, for example, TKIs against FLT3-ITD and inhibitors of anti-apoptotic signaling pathways[19].

Therefore, there is still a need for effective therapies against FLT3-ITD$^+$ AMLs, in which tumor cells are therefore positive for the FLT3-ITD mutation.

SUMMARY OF THE INVENTION

Since Tm has never been used in preclinical studies and therefore its application in a clinical trial would require several steps, the present authors replaced Tm with a proteasome inhibitor, such as, for example, the proteasome inhibitor Bortezomib (Btz, trade name Velcade), to induce ER stress and showed that the combination of low doses of ATRA, ATO and Btz is effective in inducing FLT3-ITD$^+$ AML cell death.

As mentioned above, proteasome inhibitors are known to activate UPR, and Btz is already approved by the FDA for MM treatment. Similarly, ATRA and ATO are approved and clinically used for APL treatment. The use of drugs approved by regulatory agencies, already included in therapeutic protocols, will certainly speed up the design and application of preclinical and clinical trials, with potential major effects on AML therapy.

The combination object of the present invention can be used in sequence, or in combination, with other therapies. Furthermore, it is important to emphasize that, in the studies mentioned above, the doses of drugs used were within the therapeutic dose used in other diseases, or even higher. In contrast, the present invention uses a combination of drugs which act on correlated responses to cell stresses, and this allows the use of low doses of each drug, due to a synergistic effect. This is expected to reduce systemic toxicity.

Although ATRA and ATO show a rather high safety profile at the doses currently used in APL therapy, neither of them is totally free of toxic side effects, the most important, sometimes lethal, of which being the so-called ATRA-induced differentiation syndrome[20,21]. However, doses of ATRA which are one hundred times lower[22] and doses of ATO two to ten times lower[23] than the reference therapeutic dose are used in the present invention. This makes the combination object of the present invention a potentially safe treatment without toxic side effects.

DETAILED DESCRIPTION OF THE INVENTION

Therefore, the invention relates to a composition comprising:
   a) at least one retinoid compound and/or pharmaceutically acceptable salts thereof;
   b) at least one arsenic compound; and
   c) at least one proteasome inhibitor;

for use in the treatment of acute myeloid leukemia where the tumor cells are positive for the FLT3-ITD mutation (FLT3-ITD+ AML).

The invention further relates to a product comprising:

a) at least one retinoid compound and/or pharmaceutically acceptable salts thereof;

b) at least one arsenic compound; and c) at least one proteasome inhibitor;

as a combined preparation for simultaneous, concurrent, separate or sequential use in the treatment of acute myeloid leukemia where the tumor cells are positive for the FLT3-ITD mutation (FLT3-ITD+ AML).

Preferably, the retinoid compound of the invention is all-trans retinoic acid (ATRA) and/or pharmaceutically acceptable salts thereof; further preferably, the arsenic compound is arsenic trioxide (ATO); moreover, the proteasome inhibitor is preferably selected from Bortezomib, Carfilzomib, Oprozomib, Ixazomib and Marizomib, preferably the proteasome inhibitor is Bortezomib.

The invention relates to a composition or a product as defined above wherein a) is all-trans retinoic acid (ATRA), b) is arsenic trioxide (ATO) and c) is bortezomib.

Preferably, the invention relates to a composition comprising:

a) all-trans retinoic acid (ATRA) and/or derivatives thereof and/or pharmaceutically acceptable salts thereof, b) arsenic trioxide (ATO) and c) the proteasome inhibitor Bortezomib (Btz)

for use in the treatment of acute myeloid leukemia where the tumor cells are positive for the FLT3-ITD mutation (FLT3-ITD+ AML).

The invention further relates to a product comprising:

a) all-trans retinoic acid (ATRA) and/or derivatives thereof and/or pharmaceutically acceptable salts thereof, b) arsenic trioxide (ATO) and c) the proteasome inhibitor Bortezomib (Btz)

as a combined preparation for simultaneous, concurrent, separate or sequential use in the treatment of acute myeloid leukemia where the tumor cells are positive for the FLT3-ITD mutation (FLT3-ITD+ AML).

As defined herein, a leukemia where the tumor cells are positive for the FLT3-ITD mutation is an acute myeloid leukemia (AML) with an "internal tandem duplication" mutation in the "FMS-like tyrosine kinase 3 gene" (FLT3-ITD) (FLT3-ITD+ AML). Therefore, the compositions and products defined above can be used in the treatment of FLT3-ITD$^+$ acute myeloid leukemia (FLT3-ITD+ AML).

The invention further relates to a pharmaceutical composition comprising the composition as defined herein or the product as defined herein, and at least one pharmaceutically acceptable excipient, for use in the treatment of acute myeloid leukemia where the tumor cells are positive for the FLT3-ITD mutation (FLT3-ITD+ AML). Said composition preferably comprises an agent with redox properties, preferably ascorbic acid, dehydroascorbic acid (DHA), ascorbate or melatonin.

More preferably, in the composition, product or pharmaceutical composition for use according to the invention:

a) is all-trans retinoic acid (ATRA), b) is arsenic trioxide (ATO) and c) is bortezomib.

The pharmaceutical composition of the invention is used in sequence, or in combination, with other anticancer therapies; preferably, the further anticancer therapies include idarubicin, daunorubicin, cytarabine, the anti-CD33 monoclonal antibody gemtuzumab ozogamicin and/or specific inhibitors of the FLT3 tyrosine kinase receptor.

Specific inhibitors of the FLT3 tyrosine kinase receptor include Sorafenib (DB00398; Nexavar® (Bayer)), Sunitinib [SU11248, Sutent® (Pfizer)], Lestaurtinib (CEP-701), Midostaurin (PKC412), Tandutinib (MLN518), Quizartinib (AC220), Crenolanib (CP-868-596), Gilteritinib (ASP2215), Ponatinib (AP23534), Ibrutinib (PCI-32765).

Preferably, in the composition, the product and the pharmaceutical composition according to the invention, components a), b) and c) are used in doses at which they show low toxicity when used alone.

FLT3-ITD+ AMLs respond more significantly than other subtypes (e.g., those with fusion proteins involving the MLL gene), although these other subtypes also exhibit a response. Therefore, the present invention finds application in all AMLs, preferably in FLT3-ITD+ AMLs. Components a), b) and c) are used in a therapeutically effective dosage. "Therapeutically effective dosage" of the compounds of the invention is intended to mean the dose sufficient to generate a therapeutic effect in the absence of significant side effects. The daily dose of the three active ingredients in the combination and composition according to the invention, and the daily dose of the same composition or combination, will be selected by the physician on the basis of several factors, which take into account the specific clinical picture, the characteristics of the subject under treatment, such as age and weight, the route of administration, the concurrent administration of any other drug and the duration of treatment.

The term "retinoid compound" as used herein refers to a chemical compound chemically linked to vitamin A. Examples of useful retinoid compounds include retinoic acid (RA), all-trans retinoic acid (ATRA), 9-cis retinoic acid, 13-cis retinoic acid, 9,13-di-cis retinoic acid, benzoic acid-terminated retinoids and heterocyclic analogues thereof, such as TTNPB, TTAB, AM80, AM580, SRI 1251, SRI 1247, CD666, CD367, chalcone-4-carboxylic acids, flavone-4'-carboxylic acids, etc. (Loeliger et al., 1980, Eur. J. Med. Chem-Dhim. Ther. 15: 9), (Kagechika et al, 1989, J. Med. Chem. 32: 834), (Dawson, et al. 1995, J. Med. Chem. 38: 3368) and naphthalene carboxylic acid-terminated retinoids such as TTNN, CD437, CD417 or adapalene (Dawson et al., 1983, J. Med. Chem. 26: 1653), (Dhar et al., 1999, J. Med. Chem. 42: 3602) and many other carboxylic acid retinoids (AGN 190299 or tazarotenic acid and RQ 10-9359 or acitretin). Preferably, the retinoid compound used in the present invention is all-trans retinoic acid (ATRA) and/or derivatives thereof and/or pharmaceutically acceptable salts thereof. As used herein, the term "pharmaceutically acceptable salts" refers to salts which maintain the efficacy and biological properties of the compounds of this invention and which typically are not biologically or otherwise undesirable. Inorganic bases from which salts may be derived include, for example, ammonium salts and metals from columns I to XII of the periodic table. In certain embodiments, the salts are derived from sodium, potassium, ammonium, calcium, magnesium, iron, silver, zinc and copper; particularly suitable salts include ammonium, potassium, sodium, calcium and magnesium salts. Organic bases from which salts may be derived include, for example, primary, secondary, and tertiary amines, substituted amines including naturally occurring substituted amines, cyclic amines, ion exchange basic resins, and the like. Certain organic amines include isopropylamine, benzathine, cholinate, diethanolamine, diethylamine, lysine, meglumine, piperazine and tromethamine. The term trans-retinoic acid derivatives, as used herein, includes carboxylic acid esters and/or other carboxylic acid derivatives.

As used herein, the term "arsenic compound" is intended to include arsenic and any compound having the same biological properties as arsenic. The term "compound having the same biological properties as arsenic" is intended to mean any compound which, like arsenic, is a phosphatase inhibitor and/or is capable of creating covalent adducts by binding with dithiol groups. In some embodiments, the arsenic compound is selected from the group consisting of arsenic, arsenic trioxide ($As_2O_3$; also referred to herein as ATO), arsenic exoxide ($As_4O_6$), melarsoprol, and an arsenic sulfur derivative. Preferably, the arsenic compound is arsenic trioxide ($As_2O_3$ or ATO). Arsenic trioxide (ATO), $AS_2O_3$, is a known chemotherapeutic agent. For example, it was marketed as the drug Trisenox for the treatment of acute promyelocytic leukemia (APL). In this case, it is conveniently supplied as a concentrate for solution for infusion, for dilution and subsequent intravenous administration, in a concentration of 2 mg/ml in single doses of 6 ml total. In another embodiment, arsenic trioxide may be formulated for oral administration[24].

The current indication for the use of arsenic trioxide involves the treatment of acute promyelocytic leukemia (APL). The therapeutic standard for use of arsenic trioxide in APL treatment is the administration of 0.15 mg per kg weight per day, intravenously at a recommended infusion rate of two hours, during the initial induction phase which continues until complete remission of the disease, but in any case for a period not exceeding 60 days. This is followed by a consolidation phase consisting of the administration of ATO at a dose of 0.15 mg per kg weight per day, intravenously at a recommended infusion rate of two hours, 5 days per week, in cycles of 4 weeks treatment followed by 4 weeks off treatment for a total of 4 cycles[20].

APL treatment with ATO is always accompanied by concomitant administration of retinoic acid (ATRA) during the induction therapy at a dose of 45 mg per m² per day, as an oral formulation divided into two equivalent doses for every day until complete remission of the disease, but without exceeding 60 days. ATRA is also administered with ATO during the consolidation therapy, with a dose of 45 mg per m² per day, as an oral formulation, in cycles of two consecutive weeks followed by 2 weeks off treatment for a total of 7 cycles[20,25].

In several clinical trials involving high-risk APL, i.e., with a blood leukocyte count above $10 \times 10^9$, ATRA and ATO were used in combination with classical chemotherapeutic agents, such as, for example, idarubicin[26], or with the anti-CD33 monoclonal antibody gemtuzumab ozogamicin[25,27]. Therefore, one or more additional active agents may be present in the products, pharmaceutical compositions and kits of the present invention.

Proteasome inhibitors (PIs) are molecules that block the action of the proteasome, which is a cell complex that cleaves proteins into peptides and plays an active role in normal cell functions and in the degradation of mutated or improperly folded proteins. Proteasome inhibitors are an important class of drugs for the treatment of blood cancers, including particularly multiple myeloma and mantle cell lymphoma. Bortezomib is a molecule capable of freely penetrating the cell membrane, it selectively and reversibly inhibits the activity of the 20S subunit of the proteasome complex and is the first proteasome inhibitor approved for the treatment of multiple myeloma (1 mg powder for solution for injection is administered intravenously at the recommended dose of 1.3 mg/m² body surface area twice weekly for two weeks on days 1, 4, 8 and 11 in a 21-day treatment cycle). Recently, carfilzomib, a second generation PI, has been approved by the Food & Drug Administration (FDA) for the treatment of patients undergoing at least two lines of therapy, including an immunomodulatory compound (IMiD) and bortezomib. Carfilzomib, available for intravenous administration, unlike bortezomib, binds to its target irreversibly and exhibits no significant neurological toxicity. The efficacy demonstrated in patients at relapse also allowed the testing of carfilzomib in newly diagnosed patients, both young and elderly, for the definition of new therapeutic standards. Next generation proteasome inhibitors, in a more or less early phase of the trial, are molecules such as oprozomib, ixazomib and marizomib (source: https://www.ematologiainprogress.it/i-nuovi-farmaci-nel-mieloma-multiplo/).

The active ingredients of the invention can be combined with pharmaceutically acceptable excipients, and optionally with sustained release matrices, such as biodegradable polymers, in order to form pharmaceutical compositions. As used herein, the term "pharmaceutically acceptable" means molecules and compositions which do not produce an adverse, allergic or otherwise unexpected reaction upon administration to a subject. As used herein, the terms "pharmaceutically acceptable carrier" or "pharmaceutically acceptable excipient" mean, for example, a non-toxic liquid, solid or semi-solid solvent, a diluent, an encapsulating material or an auxiliary formulation of any type. Generally, the carrier is a solvent or a dispersion medium containing, for example, water, ethanol, a polyol (such as, for example, glycerol, propylene glycol, liquid polyethylene glycol, and the like), suitable mixtures thereof and vegetable oils. The proper fluidity of the composition can be maintained by using, for example, a coating, such as lecithin, maintaining the required particle size in case of dispersion and using surfactants. Various antibacterial and antifungal agents, for example, parabens, chlorobutanol, phenol, sorbic acid, thimerosal, and similar compounds, can also be added to the composition to prevent the action of microorganisms. In many cases, it will be preferable to add isotonic agents, e.g., sugars or sodium chloride. Sustained absorption of injectable compositions can be obtained by using in the composition absorption delaying agents, such as, for example, aluminium monostearate and gelatin.

Preferably, the composition or combination of active ingredients according to the present invention includes an agent with redox properties. Redox agents are chemical substances (molecules, ions, radicals) or physical agents which, by acting as antioxidants, can slow down or prevent the oxidation of other substances, or vice versa, by disrupting the redox balance, can cause an increase in the oxidation of other molecules. Too low or too high levels of antioxidants cause oxidative stress and can damage or kill cells. Agents with redox properties include ascorbic acid and salts thereof (ascorbate), its oxidized form dehydroascorbic acid (DHA), glutathione, melatonin, tocopherols and tocotrienols, and the like (Tian T et al., Theranostics 2019, 9(13):3768; Schoenfled J. D. 2018 Semin Radiat Oncol 29:25-32; Ngo B. et al., 2019 Nature Rev Cancer 19:271).

BRIEF DESCRIPTION OF THE DRAWINGS

The present invention will now be illustrated by way of non-limiting examples with reference to the following figures.

MATERIALS AND METHODS

Cell Lines, Cultures and Treatments

Figure 1:
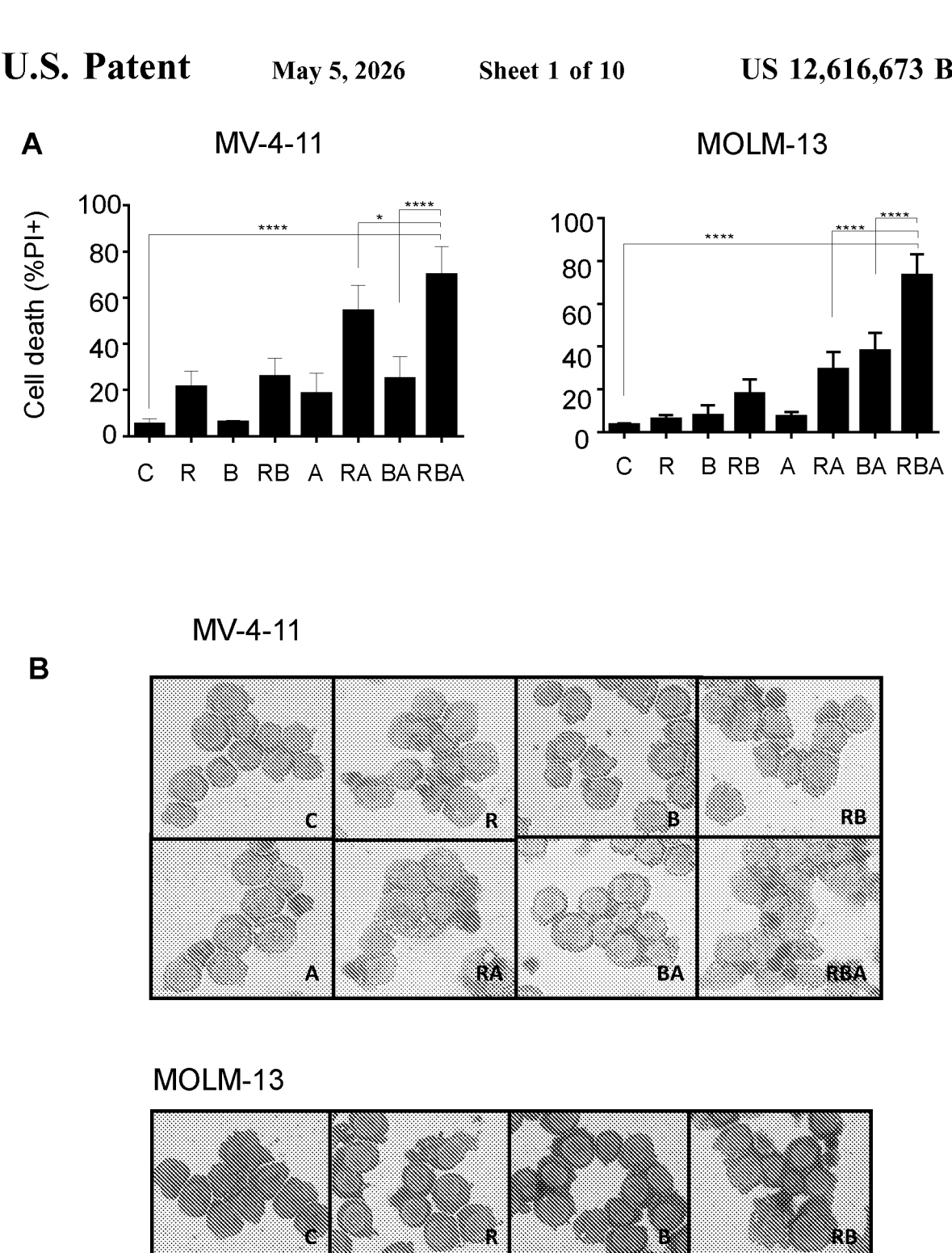
FIG. 1. Cells of the MV-4-11 cell line were treated with 10 nM ATRA (R), 1.5 nM Btz (B) and 500 nM ATO, alone or in combination as indicated. A After 72 hours from the treatment, cell death was assessed by the propidium iodide (PI) exclusion method, as measured by flow cytometer (n=6±SEM, one way ANOVA statistical analysis). Cells of the MOLM-13 cell line were treated and analysed in the same manner, except for the concentration of Btz, which in this case is 2.25 nM (n=6±SEM, one way ANOVA statistical analysis). B The morphological analysis of the treated cells confirms cell death especially in RBA-treated cells.

The MV4-11 (cat. no.: CRL-9591) and MOLM-13 (cat. no.: ACC 554) cell lines used were purchased from ATCC (Manassas, Virginia, USA) and DSMZ (Branuschweig, Germany), respectively, and kept in suspension culture in RPMI 1640 (Gibco, ThermoFisher Scientific, Waltham, MA, USA) supplemented with penicillin (50 U/ml)/streptomycin (50 μg/ml) (Gibco, ThermoFisher Scientific, Waltham, MA, USA), 2 mM L-glutamine (Gibco, ThermoFisher Scientific, Waltham, MA, USA) and 10% fetal bovine serum (FBS) (Gibco, ThermoFisher Scientific, Waltham, MA, USA), in an incubator at 37° C., in a 5% CO2 humid atmosphere. Cells were treated as indicated with 10 nM retinoic acid (RA, Sigma-Aldrich, St. Louis, MO) and/or 500 nM arsenic trioxide (ATO, Sigma-Aldrich, St. Louis, MO) and/or 1.5 or 2.5 nM Bortezomib (Btz, Med Chem Express, NJ, USA) as indicated in the figure. N-acetylcysteine, at a concentration of 20 mM (NAC, Sigma-Aldrich, St. Louis, MO) was added 24 hours before starting treatment and again when adding RA, ATO and Btz. Equivalent amounts of DMSO were added in order to have the same DMSO concentration in all samples, including the control. Primary cells were isolated at the Tor Vergata Polyclinic from FLT3-ITD+ AML patients, with prior informed consent and according to the protocol approved by the PTV Ethics Committee. These were cultured for 7 days in Stem Cell Spam leukemic cell expansion medium (STEMCELL technologies, UK) according to the manufacturer's instructions and treated with 10 nM retinoic acid (RA, Sigma-Aldrich, St. Louis, MO) and/or 500 nM arsenic trioxide (ATO, Sigma-Aldrich, St. Louis, MO) and/or 3 nM Bortezomib (Btz, Med Chem Express, NJ, USA) as shown in the figure, in the same medium.

Death, Measurement of Reactive Oxygen Species (ROS) and Cell Differentiation

Cell counts were performed by optical microscope counting in a Burker chamber, excluding dead cells by Trypan Blue staining. Cell death was assessed by flow cytometry (Cytoflex, Beckman Coulter) after staining the cells with 2.5 μg/ml propidium iodide (Sigma-Aldrich, St. Louis, MO, USA), a dye that can only penetrate dead cells. Reactive oxygen species (ROS) were measured by flow cytometry after incubation with the ROS-specific dye CM-H2DCFDA (Thermo Fisher Scientific, Waltham, MA, USA) at a concentration of 2 μM, following the manufacturer's instructions. Nrf-2 fluorescence in the nuclei was assessed by flow cytometry after isolating the nuclei as described for the preparation of the cytosolic lysate for the Western blot. Then, instead of being lysed, the nuclei were fixed with 4% paraformaldehyde for 7 min, permeabilized with 0.1% TritonX100 in PBS/1% BSA for 5 min and stained with the primary anti-Nrf-2 antibodies (rabbit monoclonal, (D1Z9C) XP® Rabbit mAb #12721, Cell Signaling Technologies, Danvers, MA, USA) and then with an Alexa Fluor-488 secondary anti-rabbit IgG antibody (Molecular Probes, ThermoFisher Scientific, Waltham, MA, USA). The DNA was stained with the Sytox Blue dye (molecular Probes, ThermoFisher Scientific, Waltham, MA, USA). Cell differentiation was assessed by morphological analysis of cell preparations by cytospin (Shandon, Thermo Fisher Scientific, Waltham, MA, USA), obtained by centrifuging approximately 250,000 cells per slide, which were then stained by the Wright-Giemsa method (Sigma-Aldrich). The preparations were analysed under a Zeiss Axioskop 2 microscope and the images were acquired with an AxioCam HRc camera and analysed using the Axiovision 4.8 software (Zeiss, Oberkochen, Germany).

Immunofluorescence.

After being deposited on a slide via cytospin, the cells were fixed with 4% paraformaldehyde for 7 min, permeabilized with 0.1% TritonX100 in PBS/1% BSA for 5 min and stained with the primary anti-FLT3 (rabbit monoclonal, FLT3 (8F2), #3462, Cell Signaling Technologies, Danvers, MA, USA) or anti-calnexin (CNX, rabbit polyclonal AB22595, AbCam, Cambridge, UK) or anti-calreticulin (CRT, rabbit polyclonal AB2907, AbCam, Cambridge, UK) or anti-LC3 (LC3B Antibody #2775) antibodies, and then with an Alexa Fluor-488 secondary anti-rabbit IgG antibody Molecular Probes, ThermoFisher Scientific, Waltham, MA, USA); the DNA was detected with the TOPRO-3 (Molecular Probes, ThermoFisher Scientific, Waltham, MA, USA) or Hoechst dye (Molecular Probes, ThermoFisher Scientific, Waltham, MA, USA) and the slides were mounted with the Vectashield medium (Vector Laboratories, Burlingame, CA, USA). The images were acquired with a Leica confocal laser scanning microscope TCS SP2 at 40× magnification or with a Zeiss LSM900 at 63× magnification. The images were analysed using the Leica Confocal software (Leica, Milan, Italy) or the Zeiss Zen Blue software.

RNA Extraction and Quantitative Real-Time PCR (qRT-PCR)

Total RNA was extracted using the TRIzol RNA Isolation System (Invitrogen) according to the protocol provided by the manufacturer. The reverse transcription was carried out using the High Capacity RNA-to-cDNA kit (Applied Biosystems) and the obtained cDNA was amplified by quantitative real time PCR (qRT-PCR) with the ABI PRISM 7000 Sequence Detection System (Applied Biosystems) using the following primers: CHOP_for 5'-GAGTCCGCA-GCAGGTGC-3' (SEQ ID NO:1), CHOP_rev 5'-TGTGACCTCTGCTGGTTCTG-3'(SEQ ID NO:2); sXBP1_for 5'-GAGTCCGCAGCAGGTGC-3'(SEQ ID NO:3), sXBP1_rev 5'-TCCTTCTGGGTAGACCTCTGG-GAG-3'(SEQ ID NO:4); BiP_for 5'-TAGCGT-ATGGTGCTGCTGTC-3'(SEQ ID NO:5), BiP_rev 5'-TTTGTCAGGGGTCTTTCACC-3'(SEQ ID NO:6); H3_for 5'-GTGAAGAAACCTCATCGTTACAGGC-C-TGGT3' (SEQ ID NO:7), H3_rev5'CTGCAAAGCAC-CAATAGCTGCACTCTGGAA-3'(SEQ ID NO:8). Data analysis was performed using the ΔΔCt method with the histone 3 (H3) gene as a normalizer. Amplification of the HMOX gene was carried out by using the PrimeTime Std qPCR Assay (Integrated DNA Technologies, Skokie, Illinois, USA) consisting of the primers: for: -TCATGAG-GAACTTTCAGAAGGG-rev (SEQ ID NO:9): -TGCGCT-CAATCTCCTCCT-(SEQ ID NO:10) and of the probe (/56-FAM/AAGGTCGGA/ZEN/GTCAACGGATTTGGTC/3IABkFQ/(SEQ ID NO:11)). In this case, the normalizer used was the housekeeping gene GAPDH: for: -ACATC-GCTCAGACACCATG-rev (SEQ ID NO:12): -TGTAGT- TGAGGTCAATGAAGGG-(SEQ ID NO:13) and the probe used was (/56 FAM/AAGGTCGGA/ZEN/GTCAACGGAT-TTGGTC/3IABkFQ/). These reactions were carried out by using the TaqMan Universal PCR Master Mix reagent (Applied Biosystems, ThermoFisher Scientific, Waltham, MA, USA).

Western Blot

The cells were lysed in two steps in order to obtain a cytosolic lysate and a nuclear lysate. For the cytosolic lysate, they were incubated for 15 min on ice in a buffer composed of 150 mM NaCl, 10 mM Hepes, 0.25% Sodium Deoxycholate, 1% NP40, 0.1% SDS, and the supernatant was recovered after centrifugation for 5 min at 300×g. The residual nuclear fraction was extracted by incubation with a buffer composed of 150 mM NaCl, 10 mM Hepes and 2% SDS, and sonicated. 40 µg of each lysate were subjected to SDS-PAGE, after boiling for 5 min with 50 mM DDT. After transferring to nitrocellulose, the proteins were stained with anti-Nrf2 antibody (rabbit monoclonal, (D1Z9C) XP® Rabbit mAb #12721, Cell Signaling Technologies, Danvers, MA, USA) and images of the blots were obtained by ChemiDoc XRS+, using the Image Lab software (Bio-Rad, Hercules, CA, USA). For LC3 expression analysis, the cytosolic and nuclear lysates were combined to obtain a total lysate, and the anti-LC3 antibody (LC3B Antibody #2775) was used.

Toxicity Analysis of the RBA Combination

Wt C56BL/6 mice were treated with 70 mg/kg R, 0.5 mg/kg B and 3 mg/kg A for three weeks according to the following regimen. Retinoic acid: administered via 10 mg subcutaneous pellets, which delivers a daily amount of 0.5 mg for 21 days. Bortezomib: administered intraperitoneally, 0.5 mg/Kg (in 100 µl saline) for 3 weeks (every 4 days). ATO: administered intraperitoneally, 3 mg/Kg (in 100 µl saline) for 3 weeks (at 5-day cycles of administration followed by 2 days without administration).

Example 1

Results

Figure 2:
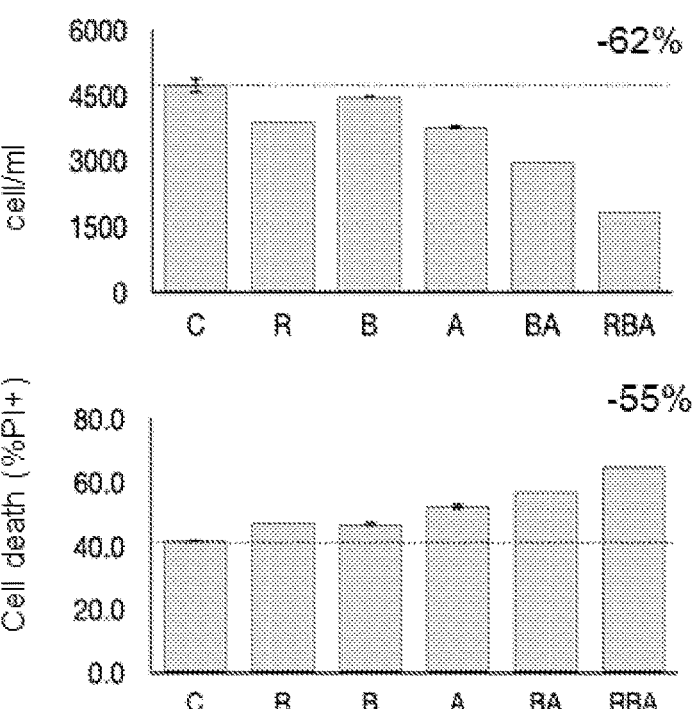
FIG. 2. Leukemic cells from two FLT3-ITD+ AML patients were isolated, amplified in culture, and treated with the indicated drugs for 7 days (C: untreated Control. R: 10 nM Retinoic acid, B: 3 nM Bortezomib, A: 500 nM Arsenic trioxide). The upper panels show the density of live cells at the end of the treatment, whereas the lower panels show the percentage of dead cells, as assessed by flow cytometry analysis. Treatment with the RBA combination can be seen to strongly slow down cell proliferation and induce death.
Figure 2:
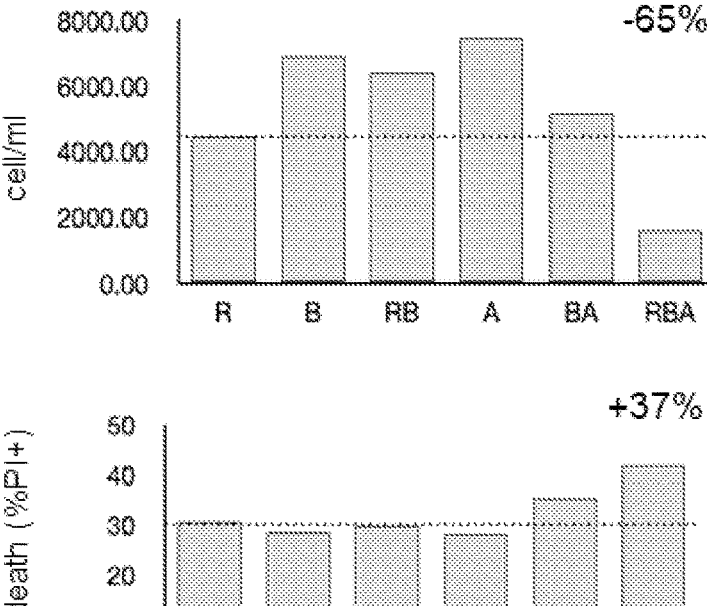
Figure 3A:
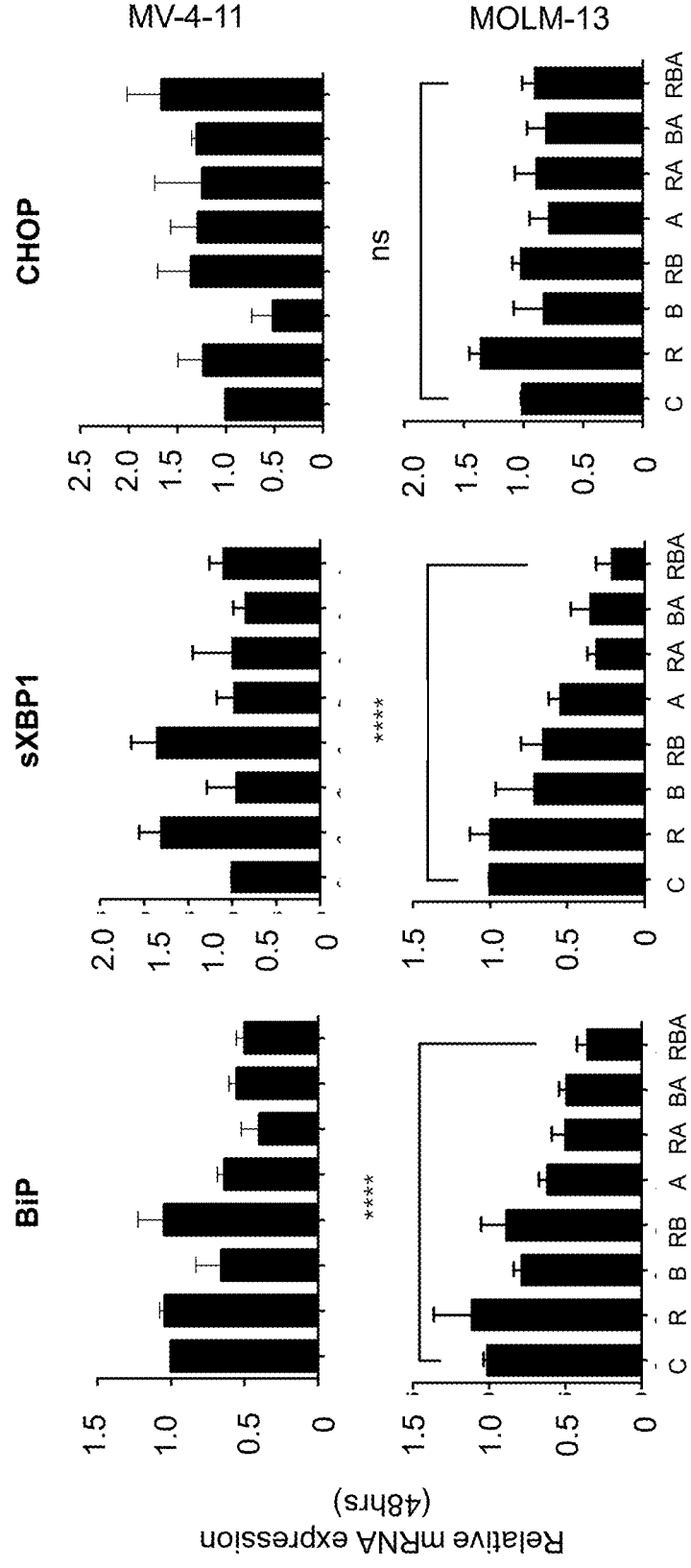
FIG. 3. A Cells of the MV-4-11 and MOLM-13 cell lines were treated as in FIG. 1A for 48 hours and the RNA was analysed by qRT-PCR to assess the expression of the UPR target genes, BiP, spliced XBP1 and CHOP (n=3±SEM, one way ANOVA statistical analysis). B Analysis of the expression and localization of the ER chaperones calnexin (CNX) and calreticulin (CRT), in green, by immunofluorescence confocal microscopy, in MV-4-11 and MOLM-13 cells exposed to treatments as in FIG. 1A. The DNA is highlighted in blue by the TO-PRO-3 dye. White arrows indicate where CNX distribution is particularly changed. C MOLM-13 cells were treated as in FIG. 1A for 24 or 48 hours. At the end of the treatment, expression of the active, lipidated form of LC3 was assessed by Western blot analysis (upper panel). The lower panel depicts the ratio between the Western blot signals from the LC3-II form (active) and the LC3-I form (inactive). D The same cells analysed by Western blot in C were also assessed by confocal microscopy analysis to highlight the LC3 dots (in green); the DNA is highlighted in blue by the Hoechst dye.

The experimental data obtained by the present authors demonstrate that the combination of ATRA, Btz and ATO, at doses at which they show low toxicity when used alone, induces a high mortality rate in the FLT3-ITD⁺ MV-4-11 AML human line; the greatest effect was obtained by using the triple combination which induces the same mortality pattern as that obtained with the combination of ATRA, Tm and ATO. The data was confirmed in a second FLT3-ITD⁺ line, the MOLM-13 line (FIGS. 1a and b). The same combination has been found to be effective in stopping proliferation and inducing cell death in FLT3-ITD+ AML cells isolated from the bone marrow of patients at diagnosis and cultured and treated ex vivo, as shown in FIG. 2. The present authors verified the working hypothesis by checking for the presence of ER stress following the combined treatments. The working hypothesis predicts that the RBA combination generates an impaired cellular protein homeostasis (also called proteostasis). In fact, the proteasome inhibitor Bortezomib (B), by inhibiting the degradation of the improperly folded proteins, causes the retention thereof in the endoplasmic reticulum (ER) with an increase in the stress of the latter and consequent activation of the Unfolded Protein Response (UPR). Arsenic trioxide (A) is a known oxidizing agent and therefore increases the oxidative stress of the cell. However, these cellular responses are activated entirely or in part according to the general state of cellular proteostasis, on the maintenance of which numerous, widely interconnected responses to cellular stresses (UPR, oxidative stress response, heat shock response, autophagy, ubiquitin-proteasome system . . . ) intervene, the activation of which is linked to threshold stress values. Therefore, we tested the activation of UPR following treatment with single drugs and the various combinations of drugs. UPR is an adaptive response aimed at recovering cellular homeostasis, but if the stress is too strong or prolonged it leads to cellular apoptosis. Of the many genes activated during UPR, some favour the adaptive response (such as BiP and sXBP-1), whereas others cause apoptosis (CHOP). Our experiments show, more clearly in MOLM-13 than in MV-4-11, that the treatments, used in double and triple combinations, cause a reduction in the expression of the genes involved in the adaptive response, without significantly altering the expression of those involved in the pro-apoptotic response (FIG. 3A). This result suggests that the impairment of the proteostasis obtained with the various combinations does not activate the adaptive UPR, consistent with the high rate of cell death.

Figure 3B:
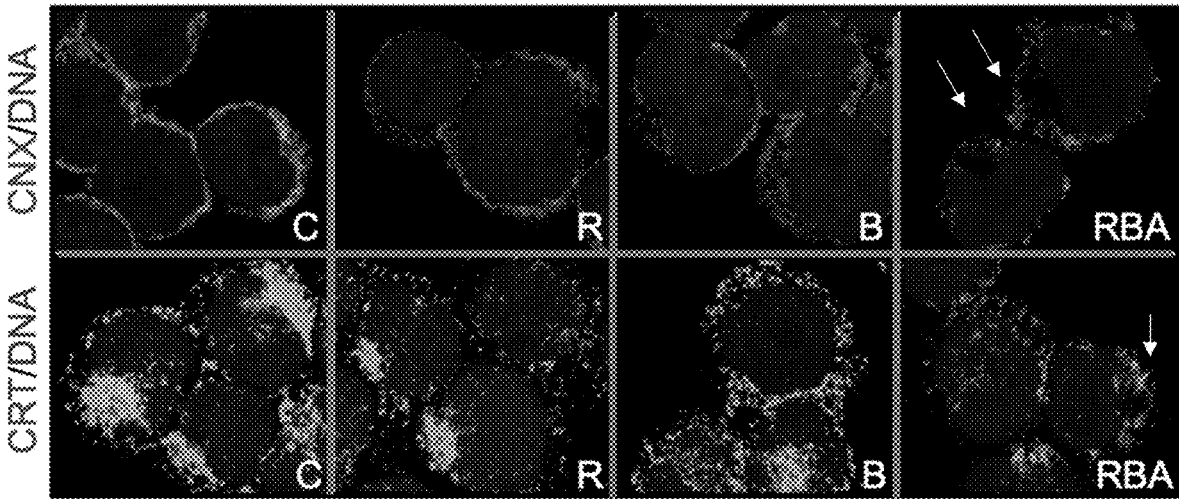
Figure 3B:
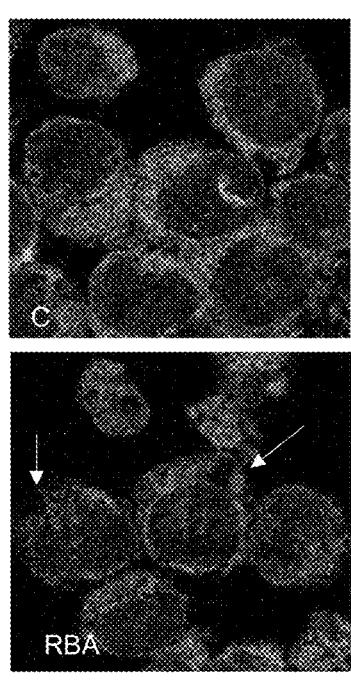

Accordingly, the distribution of two important ER chaperones, calnexin (CNX) and calreticulin (CRT), is significantly modified, particularly in RBA-treated samples, suggesting major damage to the ER (FIG. 3B), thus confirming the authors' hypothesis.

Figure 3C:
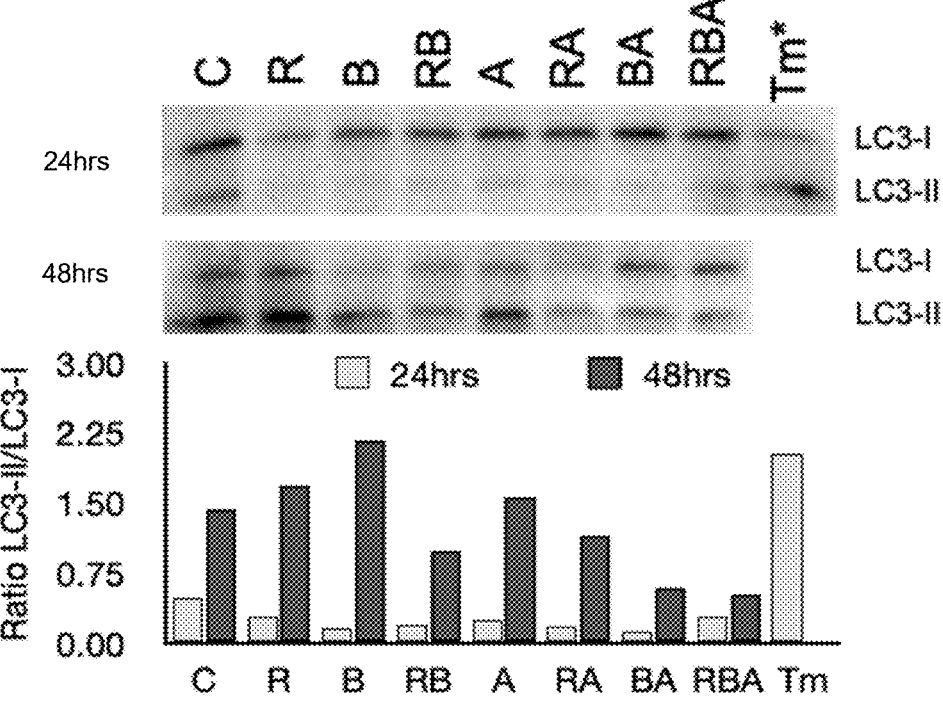
Figure 3D:
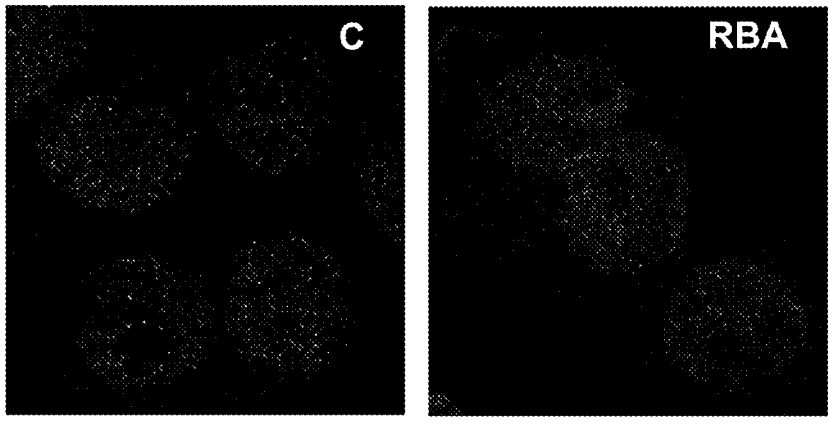

In a context of proteostasis impairment, another adaptive response that can intervene is autophagy, which is known to compensate for the inhibition of the proteasomal degradation pathway. However, the evaluation of autophagy activation in MOLM-13 cells treated with the RBA combination showed that this is not the case since, although a slight increase in LC3 activity is observed after 48 hours in culture in the control samples and in those treated with R, this is less evident in cells treated with the various combinations, in particular with BA and RBA. The probable reason why an increase in autophagy is observed in the other samples after 48 hours in culture is the high proliferation rate of these cells, which consequently rapidly deplete the nutrients present in the medium (FIGS. 3C and D).

Example 2

Figure 4A:
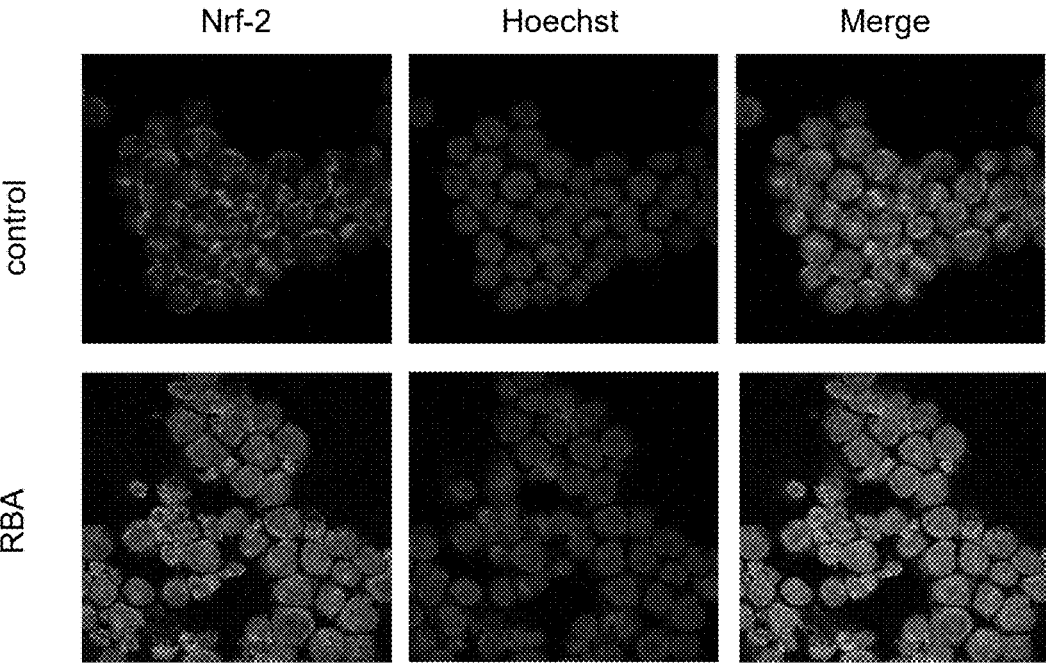
FIG. 4. A Analysis of the expression and localization of the Nrf-2 protein (in green), by immunofluorescence confocal microscopy, in MOLM-13 cells exposed to RBA treatment for 48 hours. The DNA is highlighted in blue by the Hoechst dye. B Flow cytometry analysis of Nrf-2 expression in the nuclei of MOLM-13 cells treated with the RBA combination for 48 hours by flow cytometry. The left panels show DNA staining, through which it is also possible to assess cell distribution in the various phases of the cell cycle and the presence of numerous cells in sub-G1, therefore apoptosis, after treatment with RBA. The right panels depict the fluorescence due to the anti-Nrf2 antibody, and the percentages indicate the amount of cells with the highest levels of fluorescence. C Western blot assessment of the translocation of the Nrf-2 protein from the cytosol to the nucleus in MOLM-13 cells exposed to RBA treatment for 48 hours. Cells were treated with $H_2O_2$ (100 μM for 30 minutes) or Tunicamycin (Tm, 350 nG/ml 0/N) as positive controls for Nrf-2 activation. D qRT-PCR analysis of the expression of the HMOX gene in MV-4-11 and MOLM-13 cells treated as in FIG. 1A for 24 hours (n=3±SEM, one way ANOVA statistical analysis). E Flow cytometry analysis of ROS levels in MV-4-11 and MOLM-13 cells treated with RBA for 48 hours. F MV-4-11 and MOLM-13 cells were treated as described in FIG. 1A in the presence (NAC) or absence (nil) of the reducing agent N-acetylcysteine (NAC). After 48 hours from the treatment, cell death was assessed by the propidium iodide (PI) exclusion method, as measured by flow cytometer (n=3±SEM, one way ANOVA statistical analysis). G Assessment of ROS levels, shown as the ratio to the nil control, in MOLM-13 cells treated with RBA in the presence or absence of NAC for 48 hours.
Figure 4B:
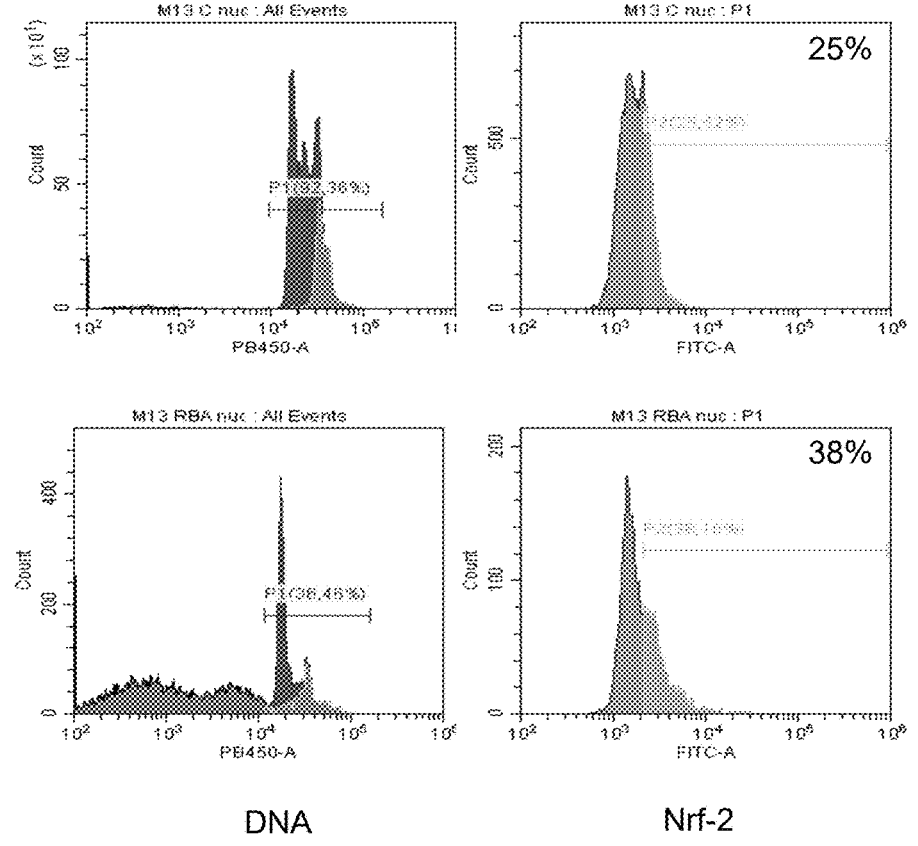
Figure 4C:
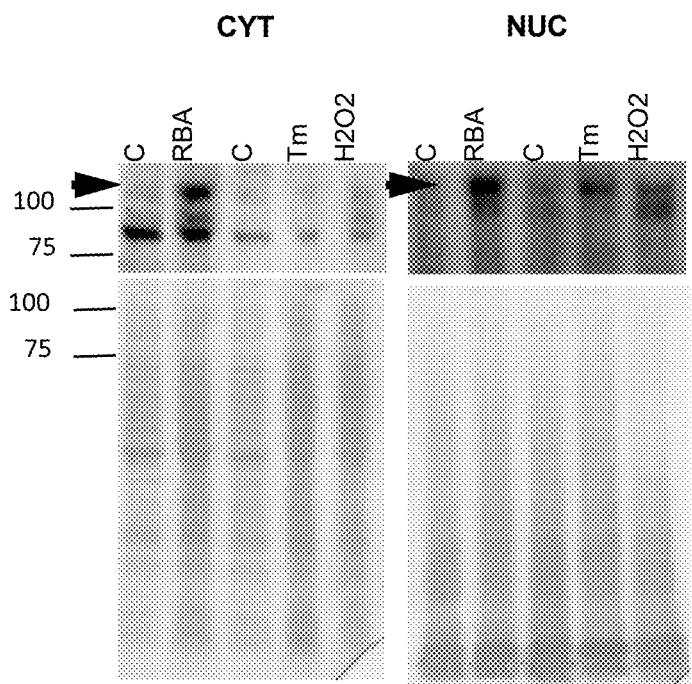
Figure 4D:
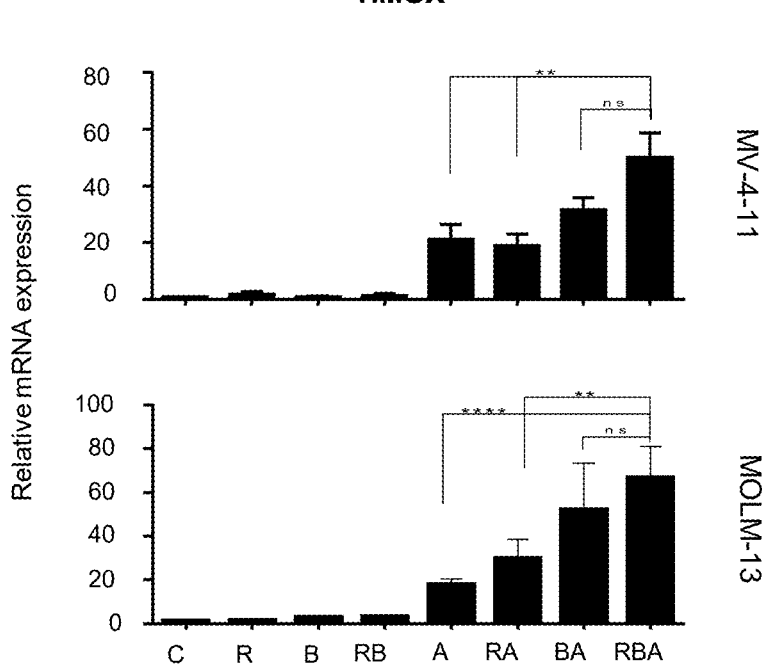
Figure 4E:
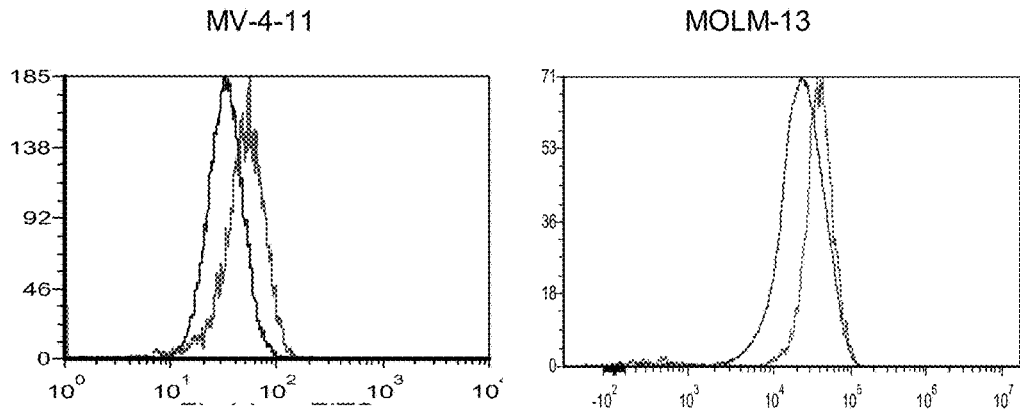
Figure 4F:
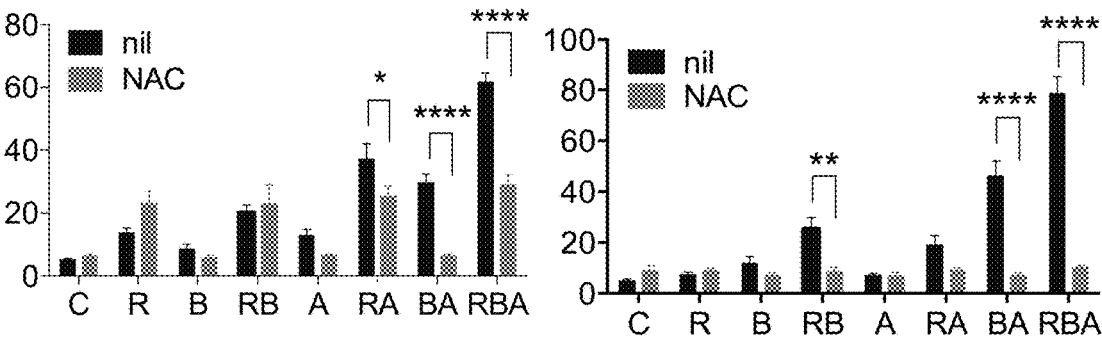
Figure 4G:
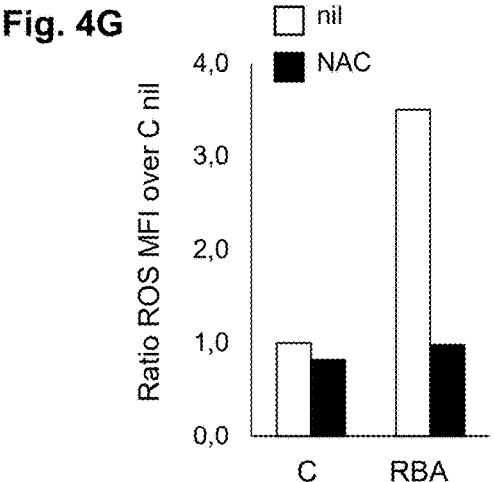

Based on studies previously published by the authors of the invention with the combination of trans-retinoic acid, Tunicamycin and arsenic trioxide (RTA), wherein ER stress was induced by the glycosylation inhibitor Tunicamycin, RBA treatment was expected to induce oxidative stress. Accordingly, oxidative stress induction was assessed in the course of the present invention. Indeed, immunofluorescence tests show that the Nrf-2 protein, i.e., the master gene that regulates the response aimed at contrasting the oxidative stress, translocates to the cell nucleus, and is then activated, following RBA treatment in MOLM-13 cells (FIGS. 4A, B and C). In accordance with the activation of the oxidative stress response triggered by Nrf-2, both MV-4-11 and MOLM-13 cells show a strong increase in the expression of the HMOX gene, an Nrf-2 target gene, in particular following the combined RBA treatment (FIG. 4D). Nrf-2 pathway activation indicates the presence of high levels of oxidative stress: in fact, the RBA combination increases the amount of reactive oxygen species (ROS) in both MV-4-11 and MOLM-13 cells (FIG. 4E). Like autophagy, the UPR is also not activated but, on the contrary, the expression of its target genes is reduced, whereas a high level of oxidative stress is observed; this leads to hold the latter probably responsible for the toxic effects of the RBA combination. We therefore incubated MV-4-11 and MOLM-13 cells with a reducing agent, N-acetylcysteine (NAC) in order to increase the reducing power of the cells, before and during treatment with the RBA combination, and this was sufficient to completely eliminate the toxic effect in MOLM-13 cells and to partially eliminate it in MV-4-11 cells (FIG. 4F). This difference is probably due to the fact that MV-4-11 cells are sensitive to R even when it is used alone; this result indicates that the toxicity of R alone is independent of the generation of oxidative stress, whereas, on the other hand, the toxicity caused by the synergy with B and A depends on it, since the mortality rate of cells treated with RBA, in the presence of NAC, is comparable to that of cells treated with R alone. The ability of NAC to decrease the oxidative stress level has been demonstrated in MOLM-13 cells in which, in the presence of NAC, the amount of ROS remains the same as in control cells even after treatment with RBA (FIG. 4G). The use of NAC demonstrates that the toxicity of the RBA combination is due to the generation of oxidative stress, which is linked to proteostasis impairment. In fact, as mentioned above, the various adaptive responses required to maintain the proteostasis are closely related to each other, and the ER stress is known to increase the oxidative stress, and vice versa.

Example 3

Figure 5A:
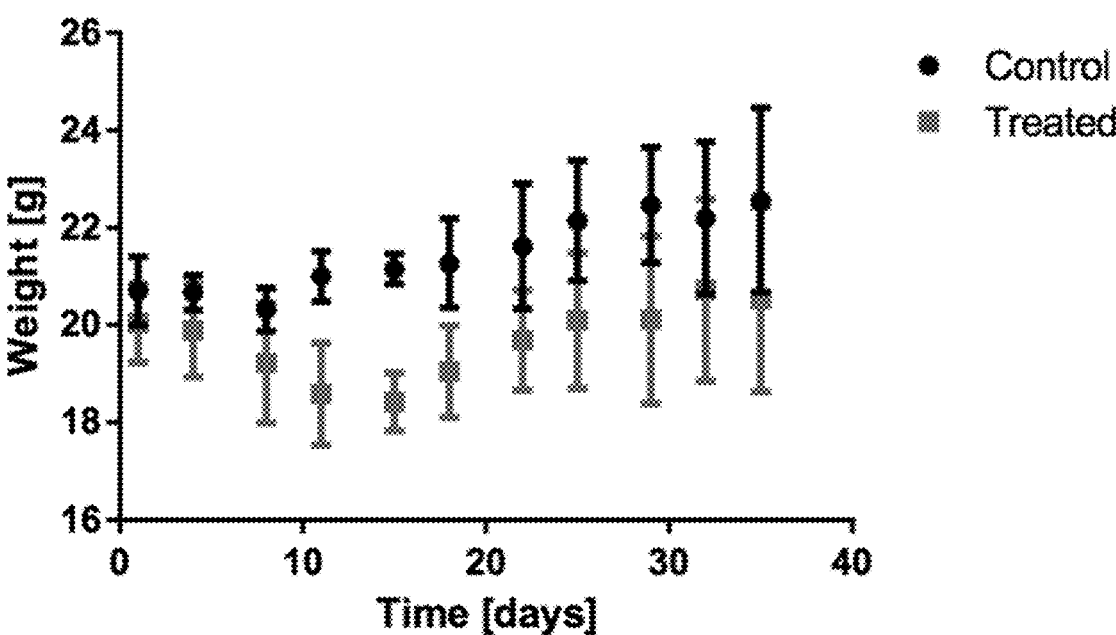
FIG. 5 Wt mice were treated for three weeks with 70 mg/kg trans-retinoic acid (R), 0.5 mg/kg Bortezomib (B) and 3 mg/kg arsenic trioxide (A). A The treatment did not significantly affect the animals' growth and weight, nor was it found to alter their behaviour. B Post-mortem analysis of the organs normally most affected by this type of drug showed no signs of toxicity.
Figure 5B:
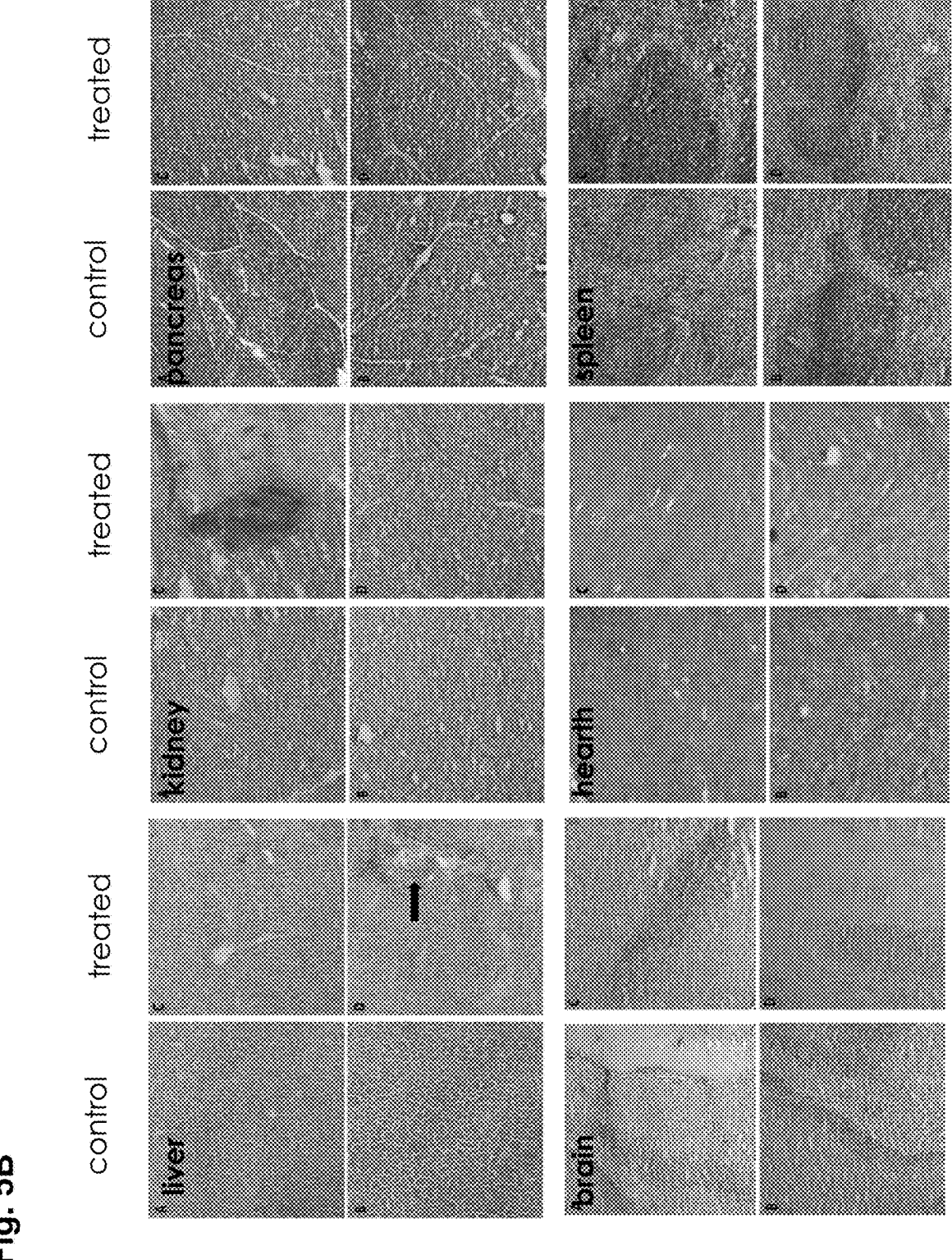

Preclinical toxicity studies were performed in wt murine models. As regards toxicity, the results lead to the conclusion that the combination, as proposed in the patent application, is not harmful to animals. In fact, no changes in the behaviour, feeding or mobility of the animals treated with the RBA combination compared to the control, nor changes in body weight are observed (FIG. 5A). Seven days after the end of the treatment, the animals were sacrificed to assess the macroscopic and microscopic state of several organs, including pancreas and liver, which could be more sensitive to any toxicity of the treatment. Both macroscopic and microscopic examinations showed no differences between the control animals and those treated with the RBA combination (FIG. 5B).

REFERENCES

1. Auner H W, Cenci S. Recent advances and future directions in targeting the secretory apparatus in multiple myeloma. *Br J Haematol.* 2015; 168(1):14-25.
2. Cenci S, Mezghrani A, Cascio P, et al. Progressively impaired proteasomal capacity during terminal plasma cell differentiation. *EMBO J.* 2006; 25(5):1104-1113.
3. Masciarelli S, Capuano E, Ottone T, et al. Retinoic acid and arsenic trioxide sensitize acute promyelocytic leukemia cells to E R stress. *Leukemia.* 2018; 32(2):285-294.
4. Lo-Coco F, Di Donato L, Gimema, Schlenk R F, German-Austrian Acute Myeloid Leukemia Study G, Study Alliance L. Targeted Therapy Alone for Acute Promyelocytic Leukemia. *N Engl J Med.* 2016; 374(12):1197-1198.
5. Schmidt-Arras D E, Bohmer A, Markova B, Choudhary C, Serve H, Bohmer F D. Tyrosine phosphorylation regulates maturation of receptor tyrosine kinases. *Mol Cell Biol.* 2005; 25(9):3690-3703.
6. Kindler T, Lipka D B, Fischer T. FLT3 as a therapeutic target in AML: still challenging after all these years. *Blood.* 2010; 116(24):5089-5102.
7. Masciarelli S, Capuano E, Ottone T, et al. Retinoic acid synergizes with the unfolded protein response and oxidative stress to induce cell death in FLT3-ITD+AML. *Blood Adv.* 2019; 3(24):4155-4160.

8. Perl A E. The role of targeted therapy in the management of patients with AML. *Blood Adv.* 2017; 1(24):2281-2294.

9. Perl A E, Altman J K, Cortes J, et al. Selective inhibition of FLT3 by gilteritinib in relapsed or refractory acute myeloid leukaemia: a multicentre, first-in-human, open-label, phase 1-2 study. *Lancet Oncol.* 2017; 18(8):1061-1075.

10. Stone R M, Mandrekar S J, Sanford B L, et al. Midostaurin plus Chemotherapy for Acute Myeloid Leukemia with a FLT3 Mutation. *N Engl J Med.* 2017; 377(5):454-464.

11. Cortes J E, Khaled S, Martinelli G, et al. Quizartinib versus salvage chemotherapy in relapsed or refractory FLT3-ITD acute myeloid leukaemia (QuANTUM-R): a multicentre, randomised, controlled, open-label, phase 3 trial. *Lancet Oncol.* 2019; 20(7):984-997.

12. Alexander E. Perl G M, Jorge E. Cortes, Andreas Neubauer, Ellin Berman, Stefania Paolini, Pau Montesinos, Maria R. Baer, Richard A. Larson, Celalettin Ustun, Francesco Fabbiano, Antonio Di Stasi, Robert Stuart, Rebecca Olin, Margaret Kasner, Fabio Ciceri, Wen-Chien Chou, Nikolai Podoltsev, Christian Recher, Hisayuki Yokoyama, Naoko Hosono, Sung-Soo Yoon, Je-Hwan Lee, Timothy Pardee, Amir T. Fathi, Chaofeng Liu, Xuan Liu, Erkut Bahceci and Mark J. Levis. Abstract CT184: Gilteritinib significantly prolongs overall survival in patients with FLT3-mutated (FLT3mut+) relapsed/refractory (R/R) acute myeloid leukemia (AML): Results from the Phase III ADMIRAL trial. *Proceedings of the American Association for Cancer Research Annual Meeting* 2019; 2019 Mar. 29-Apr. 3; Atlanta, GA Philadelphia (PA): *AACR; Cancer Res* 2019; 79(13 Suppl): *Abstract nr CT184.* 2019.

13. Larrue C, Saland E, Boutzen H, et al. Proteasome inhibitors induce FLT3-ITD degradation through autophagy in AML cells. *Blood.* 2016; 127(7):882-892.

14. Tsitsipatis D, Jayavelu A K, Muller J P, et al. Synergistic killing of FLT3ITD-positive AML cells by combined inhibition of tyrosine-kinase activity and N-glycosylation. *Oncotarget.* 2017; 8(16):26613-26624.

15. Gregory M A, D'Alessandro A, Alvarez-Calderon F, et al. ATM/G6PD-driven redox metabolism promotes FLT3 inhibitor resistance in acute myeloid leukemia. *Proc Natl Acad Sci USA.* 2016; 113(43):E6669-E6678.

16. Ma H S, Greenblatt S M, Shirley C M, et al. All-trans retinoic acid synergizes with FLT3 inhibition to eliminate FLT3/ITD+ leukemia stem cells in vitro and in vivo. *Blood.* 2016; 127(23):2867-2878.

17. Wang L N, Tang Y L, Zhang Y C, et al. Arsenic trioxide and all-trans-retinoic acid selectively exert synergistic cytotoxicity against FLT3-ITD AML cells via co-inhibition of FLT3 signaling pathways. *Leuk Lymphoma.* 2017; 58(10):2426-2438.

18. McMahon C M, Ferng T, Canaani J, et al. Clonal Selection with RAS Pathway Activation Mediates Secondary Clinical Resistance to Selective FLT3 Inhibition in Acute Myeloid Leukemia. *Cancer Discov.* 2019; 9(8): 1050-1063.

19. Moujalled D M, Pomilio G, Ghiurau C, et al. Combining BH3-mimetics to target both BCL-2 and MCL1 has potent activity in pre-clinical models of acute myeloid leukemia. *Leukemia.* 2019; 33(4):905-917.

20. Lo-Coco F, Avvisati G, Vignetti M, et al. Retinoic acid and arsenic trioxide for acute promyelocytic leukemia. *N Engl J Med.* 2013; 369(2):111-121.

21. Sanz M A, Montesinos P. How we prevent and treat differentiation syndrome in patients with acute promyelocytic leukemia. *Blood.* 2014; 123(18):2777-2782.

22. Muindi J R, Frankel S R, Huselton C, et al. Clinical pharmacology of oral all-trans retinoic acid in patients with acute promyelocytic leukemia. *Cancer Res.* 1992; 52(8):2138-2142.

23. Firkin F, Roncolato F, Ho W K. Dose-adjusted arsenic trioxide for acute promyelocytic leukaemia in chronic renal failure. *Eur J Haematol.* 2015; 95(4):331-335.

24. Au W Y, Fong B M, Tam S, Kwong Y L. Feasibility of oral arsenic trioxide treatment for acute promyelocytic leukemia during hemodialysis. *Ann Hematol.* 2013; 92(3):417-418.

25. Osman A E G, Anderson J, Churpek J E, et al. Treatment of Acute Promyelocytic Leukemia in Adults. *J Oncol Pract.* 2018; 14(11):649-657.

26. Iland H J, Collins M, Bradstock K, et al. Use of arsenic trioxide in remission induction and consolidation therapy for acute promyelocytic leukaemia in the Australasian Leukaemia and Lymphoma Group (ALLG) APML4 study: a non-randomised phase 2 trial. *Lancet Haematol.* 2015; 2(9): e357-366.

27. Abaza Y, Kantarjian H, Garcia-Manero G, et al. Long-term outcome of acute promyelocytic leukemia treated with all-trans-retinoic acid, arsenic trioxide, and gemtuzumab. *Blood.* 2017; 129(10):1275-1283.

The invention claimed is:

1. A method for treating acute myeloid leukemia in a patient having tumor cells which are FLT3-ITD mutation positive, comprising administering:
   a) all-trans retinoic acid (ATRA) and/or pharmaceutically acceptable salts thereof;
   b) arsenic trioxide (ATO); and
   c) a proteasome inhibitor, wherein the proteasome inhibitor is Bortezomib;
   to a patient in need thereof, wherein all-trans retinoic acid (ATRA) is administered at 70 mg/kg, bortezomib is administered at 0.5 mg/kg and arsenic trioxide (ATO) is administered at 3 mg/kg.

2. The method of claim 1, wherein said method is used in sequence, or in combination, with other anticancer therapies.

3. The method according to claim 2, wherein the other anticancer therapies are selected from idarubicin, daunorubicin, cytarabine, the anti-CD33 monoclonal antibody gemtuzumab ozogamicin and/or specific inhibitors of the FLT3 tyrosine kinase receptor.

4. The method of claim 1, wherein the all-trans retinoic acid (ATRA) and/or pharmaceutically acceptable salt thereof; the arsenic trioxide (ATO); and the proteasome inhibitor are administered as a combined preparation.

5. The method of claim 1, wherein the all-trans retinoic acid (ATRA) and/or pharmaceutically acceptable salt thereof; the arsenic trioxide (ATO); and the proteasome inhibitor are administered concurrently.

6. The method of claim 1, wherein the all-trans retinoic acid (ATRA) and/or pharmaceutically acceptable salt thereof; the arsenic trioxide; and the proteasome inhibitor are administered sequentially.

7. The method of claim 1, wherein the ATRA, bortezomib, and ATO are administered for a period of 3 weeks.

* * * * *